US012642751B2

(12) United States Patent
Wu

(10) Patent No.: US 12,642,751 B2
(45) Date of Patent: Jun. 2, 2026

(54) REUSABLE MULTI-PURPOSE CONTAINER FOR BREAST MILK AND FOOD STORAGE

(71) Applicant: GLBF ASSOCIATES LLC, Seattle, WA (US)

(72) Inventor: Meredith Wu, Seattle, WA (US)

(73) Assignee: GLBF ASSOCIATES LLC, Seattle, WA (US)

( * ) Notice: Subject to any disclaimer, the term of this patent is extended or adjusted under 35 U.S.C. 154(b) by 1077 days.

(21) Appl. No.: 17/727,419

(22) Filed: Apr. 22, 2022

(65) Prior Publication Data

US 2022/0339074 A1 Oct. 27, 2022

Related U.S. Application Data

(60) Provisional application No. 63/179,108, filed on Apr. 23, 2021.

(51) Int. Cl.
*A61J 9/00* (2006.01)
*A61J 11/04* (2006.01)
*A61M 1/06* (2006.01)

(52) U.S. Cl.
CPC .............. *A61J 9/005* (2013.01); *A61J 11/045* (2013.01); *A61M 1/068* (2014.02)

(58) Field of Classification Search
CPC ........ A61J 9/005; A61J 11/045; A61M 1/068; A61M 1/062; Y02W 30/80; A47G 19/2266; B65D 79/008; B65D 33/1666; A61F 5/445; A61F 5/448; A61F 2005/4486
See application file for complete search history.

(56) References Cited

U.S. PATENT DOCUMENTS

| | | | |
|---|---|---|---|
| 3,354,601 | A | 11/1967 | Schneider et al. |
| 4,541,117 | A | 9/1985 | Ashbeck |
| 5,065,923 | A | 11/1991 | Hoefer et al. |
| 5,347,671 | A | 9/1994 | Hunts |
| 5,385,251 | A | 1/1995 | Dunn |
| D374,204 | S | 10/1996 | Weder |
| D406,758 | S | 3/1999 | Bright et al. |
| D467,131 | S | 12/2002 | Wright et al. |
| D471,447 | S | 3/2003 | Sagel |
| D475,622 | S | 6/2003 | Sagel |
| D479,991 | S | 9/2003 | Bezek et al. |
| D495,607 | S | 9/2004 | Bezek |
| 7,975,868 | B1 | 7/2011 | Flies et al. |
| D667,276 | S | 9/2012 | Hager |

(Continued)

FOREIGN PATENT DOCUMENTS

| | | |
|---|---|---|
| CN | 101641072 A | 2/2010 |
| CN | 104797230 A | 7/2015 |

(Continued)

OTHER PUBLICATIONS

Design U.S. Appl. No. 29/782,170 titled "Storage Container" filed May 4, 2021.

(Continued)

*Primary Examiner* — Scott J Medway
*Assistant Examiner* — Lei Gonzalez
(74) *Attorney, Agent, or Firm* — Dorsey & Whitney LLP

(57) ABSTRACT

The present disclosure describes a breast milk and food storage solution that simplifies and reduces the number of items needed to pump, store and/or feed breastmilk to a baby.

12 Claims, 10 Drawing Sheets

(56) References Cited

U.S. PATENT DOCUMENTS

| | | | | |
|---|---|---|---|---|
| D690,881 | S | 10/2013 | Lai | |
| 9,480,625 | B2 | 11/2016 | Mcbean et al. | |
| D793,818 | S | 8/2017 | Debretton | |
| 9,789,988 | B2 * | 10/2017 | Wilson | B65D 47/0885 |
| 9,855,194 | B1 * | 1/2018 | Walter, Jr. | A61J 11/045 |
| D867,587 | S | 11/2019 | Hotlz et al. | |
| D874,876 | S | 2/2020 | Finell et al. | |
| D876,891 | S | 3/2020 | Finell et al. | |
| D944,595 | S | 3/2022 | Liao | |
| D945,827 | S | 3/2022 | Finell et al. | |
| D945,828 | S | 3/2022 | Finell et al. | |
| D970,352 | S | 11/2022 | Chan | |
| D994,500 | S | 8/2023 | Carpinelli | |
| D1,007,327 | S | 12/2023 | Carpinelli | |
| D1,035,448 | S | 7/2024 | Wu | |
| 2003/0230351 | A1 | 12/2003 | Renz | |
| 2008/0051733 | A1 * | 2/2008 | Lynn | A61B 10/0045 |
| | | | | 604/256 |
| 2014/0135683 | A1 | 5/2014 | Hradisky et al. | |
| 2015/0217911 | A1 | 8/2015 | Wilson | |
| 2019/0110956 | A1 * | 4/2019 | Smith | A61J 11/04 |
| 2020/0071035 | A1 | 3/2020 | Hanan | |
| 2021/0237937 | A1 * | 8/2021 | Ramsey | B65D 33/1666 |
| 2024/0217708 | A1 * | 7/2024 | Hanan | B29B 11/14 |

FOREIGN PATENT DOCUMENTS

| | | | |
|---|---|---|---|
| CN | 204916714 | U | 12/2015 |
| GB | 6173861 | | 11/2021 |
| JP | 2015116431 | A | 6/2015 |
| JP | 2018117884 | A | 8/2018 |
| WO | 2014059223 | A1 | 4/2014 |

OTHER PUBLICATIONS

"Aqua 6 oz Squeasy Snacker Spill Proof Silicone Reusable Food Pouch—for Both Soft Foods and Liquids—Water, Apple Sauce, Yogurt, Smoothies, Baby Food—Dishwasher Safe", Retrieved at https://www.amazon.com/Squeasy-Snacker-Spill-Silicone-Reusable/dp/B01A0XA5I8/ref=sr_1_1_sspa?, on May 5, 2021.

"Kiinde Twist Universal Direct-Pump Feeding System Starter Kit for Leak-Free and Transfer-Free Breastmilk Collection, Freezing, Heating and Feeding, New Mom Gift", Retrieved at https://www.amazon.com/Kiinde-Breast-Storage-Twist-Starter/dp/B00CXSPL24/ref=sr_1_1?crid=GN30JRO1SOWG&dchild=1&keywords=kiinde+twist+breastfeeding+starter+kit&qid=1609810252&sprefix=kiinde%2Caps%2C232&sr=8-1, on May 5, 2021.

"Playtex Baby Nurser Reusable Silicone PODS, Breastmilk Storage & Air-Free Feeding, 4 oz, 6 Count", Retrieved at https://www.amazon.com/Playtex-Reusable-Silicone-Breastmilk-Air-Free/dp/B082BWSHMF/ref=sr_1_5?dchild=1&keywords=junobie&qid=1609810085&sr=8-5, on May 5, 2021.

"Reusable Breastmilk Storage Bag (Mint) by Junobie. Food Grade Silicone Pouches to Grow with Your Baby for Milk Storage, Baby Food Pouch & Toddler Snack Pack (2-Pack, 8oz Each)", Retrieved at https://www.amazon.com/Reusable-Breastmilk-Storage-JUNOBIE-Silicone/dp/B084LW87SM/ref=sr_1_1_sspa?dchild=1&keywords=junobie&qid=1609810032&sr=8-1-spons&psc=1&spLa, on May 5, 2021.

"Reusable Milk Storage Bags from Junobie for the Win!—BeauGen Mom", Retrieved at https://www.beaugen.com/blogs/news/reusable-milk-storage-bags-from-junobie-for-the-win, on May 5, 2021.

"Zip Top Reusable 100% Platinum Silicone Breast Milk Storage, Made in the USA—Bag Set of 6 + Freezer Tray", Retrieved at https://www.amazon.com/Zip-Top-Reusable-Platinum-Silicone/dp/B08464T6LV/ref=sr_1_10?crid=27I6OW89F4SN5&dchild=1&keywords=zip+top+silicone+containers&qid=1609808573&sprefix=zip+top%2Caps%2C228&sr=8-10, on May 5, 2021.

"ZipTop Breast Milk Bag 6-Set + Freezer Tray", Retrieved at https://ziptop.com/products/milk-bag-set, on May 5, 2021.

International Search Report & Written Opinion dated Sep. 15, 2022 for PCT Application No. PCT/US2022/025970.

U.S. Appl. No. 29/782,170, Non-Final Office Action, Jun. 1, 2023, 8 pages.

* cited by examiner

REUSABLE MULTI-PURPOSE CONTAINER FOR BREAST MILK AND FOOD STORAGE

CROSS-REFERENCE TO RELATED APPLICATION

This application claims the filing benefit of U.S. Provisional Application No. 63/179,108, filed Apr. 23, 2021. This application is incorporated by reference herein in its entirety and for all purposes.

TECHNICAL FIELD

This disclosure relates generally to a reusable multi-purpose container for storing breast milk and subsequent feeding of the breast milk to the baby.

BACKGROUND

Breast milk extraction, through pumping, is an alternative method to nursing for providing breast milk to a baby. Various breast pumps and accessories have been developed over time to assist mothers with breast milk extraction and storage. However, despite the various products on the market, pumping and storing breast milk remains cumbersome and often requires numerous supplies, for the pumping process, storage process, and subsequent feeding of the breast milk to the baby. Designers and manufacturers of breast milk extraction and storage solutions, thus, continue to seek improvements thereto.

BRIEF DESCRIPTION OF THE DRAWINGS

The accompanying drawings and figures illustrate a number of exemplary embodiments and are part of the specification. Together with the present description, these drawings demonstrate and explain various principles of this disclosure. A further understanding of the nature and advantages of the present invention may be realized by reference to the following drawings. In the appended figures, similar components or features may have the same reference label.

Figure 1:
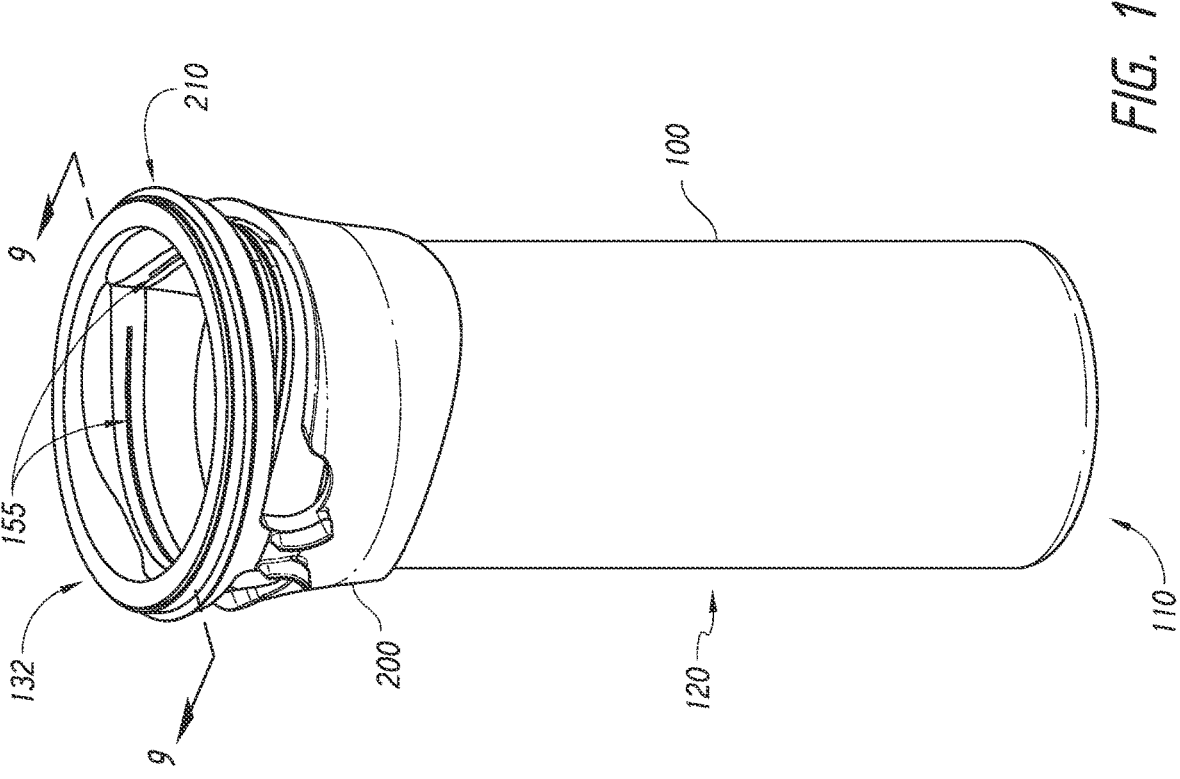
FIG. 1 is a top isometric view of a storage and feeding system according to some embodiments of the present disclosure.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

The following description of certain embodiments is merely exemplary in nature and is in no way intended to limit the scope of the disclosure or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the disclosure. Moreover, for the purpose of clarity, detailed descriptions of certain features will not be discussed when they would be apparent to those with skill in the art so as not to obscure the description of embodiments of the disclosure. The following detailed description is therefore not to be taken in a limiting sense, and the scope of the disclosure is defined only by the appended claims.

As previously noted, it is sometimes desirable to extract breast milk (e.g., by pumping) for indirectly breast feeding a baby, and optionally storing the breast milk prior to feeding it to the baby. While some solutions are available on the market, typically the pumping, storing, and feeding, and optionally heating prior to feeding, of breast milk involves the use of different containers, typically at each stage of the process, which are specifically designed for a given stage of the process, making the process not only cumbersome but often resulting in the wastage of precious breast milk. For example, numerous rigid plastic and glass bottles exist which are designed as milk container for use during pumping and/or feeding, but are generally not suitable for storage (e.g., they take up too much space) or for reheating the milk, particularly in the case of plastic bottles. Similarly, a variety of breast milk storage bags made from thin film plastic materials are available on the market, and while these bags may be well suited for storing milk they are typically unsuitable for pumping into them and/or for feeding the baby directly from them. Thus, in these scenarios, there inevitably is a need for transferring breast milk from one container designed for use with a breast pump into another container designed for efficient storage, into yet another container designed for safely heating and/or feeding breast milk, which wastes breast milk, a valuable resource of a breast feeding mother. Also the use of disposable plastic bags for storage of milk results in extra plastic waste. The present disclosure provides an all-in-one solution to this multi-stage process of indirectly breast feeding a baby.

Figure 11B:
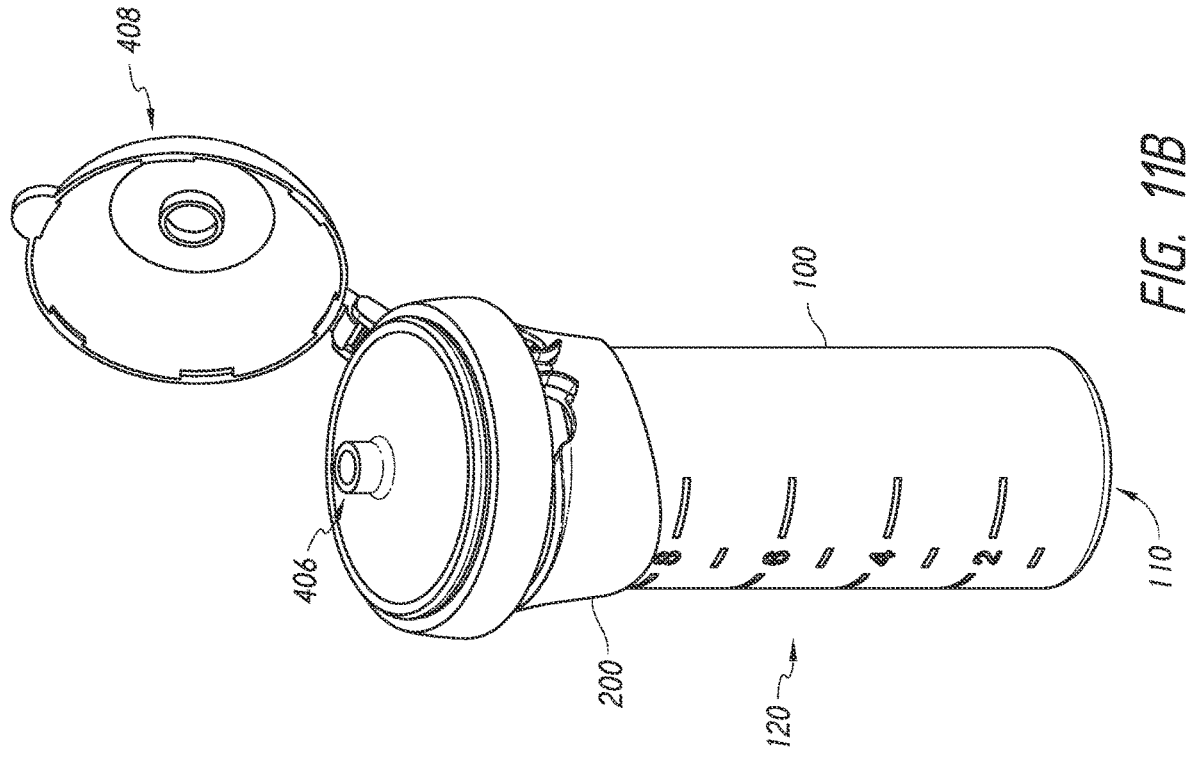
FIGS. 11A and 11B show isometric views of a container according to the present disclosure in two use configurations, with a feeding nipple and bottle cap, respectively, attached to the collar of the container.
Figure 11A:
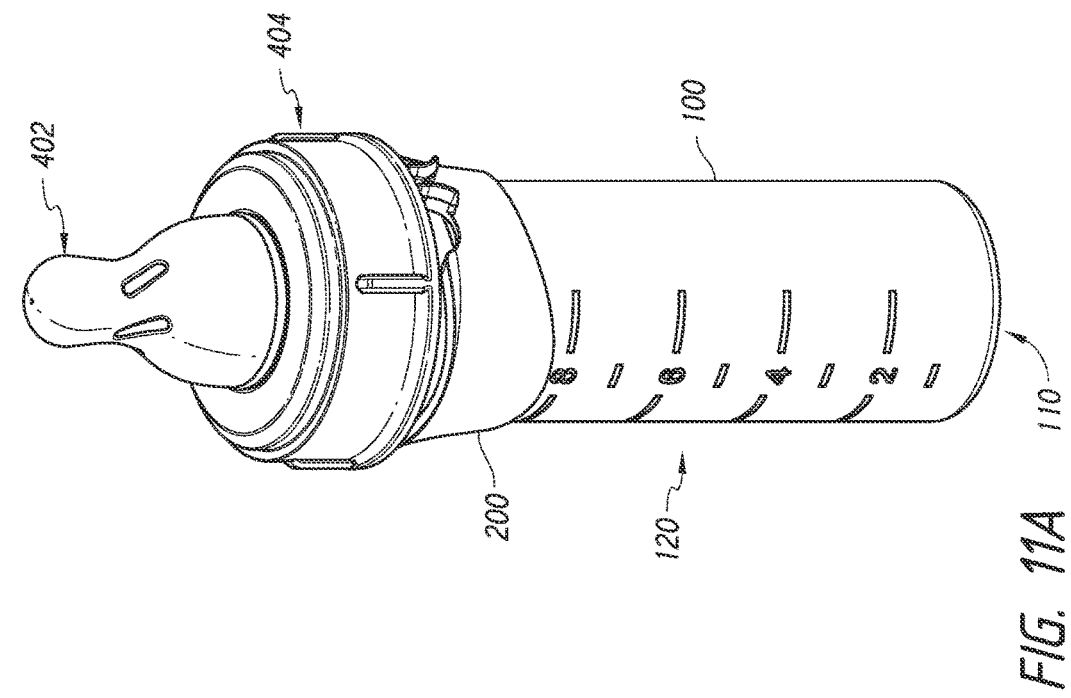

FIGS. 1-4, show views of a multi-purpose breast milk storage and feeding container according to some embodiments of the present disclosure. The breast milk storage container shown in these figures is re-usable and doubles as a feeding bottle. The container easily reconfigures between a closed configuration, also referred to as storage configuration, and an open configuration. In the storage configuration, the container is substantially sealed, by its opening being reconfigured into a closure that is leak proof and substantially air tight. When in the storage configuration, the container is usable as a leak proof and substantially air tight storage for breast milk (or other liquids and semi-liquids) in any desired environment (e.g., a refrigerator, a freezer or at room temperature). In the open configuration the container's opening or mouth is reconfigured into a substantially circular opening to enable depositing or dispensing liquid into and out of the container. In this configuration, a collar is removably attachable to the container for operatively coupling the container with various accessories (e.g., a connector or adapter of a breast pump or a feeding accessory such as a feeding bottle nipple 402 as shown for example in FIG. 11a).

In some embodiment, the container is made from a flexible (e.g., elastomeric) material, which is resiliently deformable meaning that the shape of the container can be non-plastically temporarily deformed under application of a force, the container returning to its original shape when the applied force is removed. While flexible, the container is configured to generally retain its shape and more specifically it includes, in some embodiments, a base that can stably support the container in an upright position on a support surface. Any suitable flexible material may be used, for example food grade silicone. In other embodiments, any suitable material, which is safe for use with food (e.g., breast milk or other edible liquids/semi-liquids) both at room temperature as well as above (e.g., when heating breast milk in the container, or washing the container in hot water) or below (e.g., when chilling/freezing the breast milk) room temperature, may be used. Providing the container as a flexible container may provide various advantages such as a soft texture for easy, non-slip grip or hold (e.g., by an infant), avoiding use of rigidized plastics which often contain Bisphenol A (BPA), phthalates or other harmful plastic ingredients and thus eliminating any contact of the breast milk with such plastics that can contaminate the breast milk (e.g. during storage and/or heating). In some embodiments the entire container is formed of the same flexible material (e.g., food grade silicone), for example through molding or other suitable manufacturing process. In some embodiments, the flexible material may be molded to provide a container having a substantially constant thickness throughout. In other embodiments, at least a portion (e.g., the top portion including the mouth) of the container is formed of the flexible material to enable reconfiguring between the open and closed configurations, while other portion(s) of the container (e.g., the base) may be formed of a rigid material. In some embodiments in which the entire container is integrally formed of the same flexible material, suitable material thickness, e.g., at the base, is used to provide a base that can stably support the container in an upright position onto a support surface. In some such embodiments, different thickness of material may be used for the base and elsewhere (e.g., at the mouth of the container). Rigid components of the storage and feeding system 10 (e.g., the collar and/or clamp) may be made from any suitable material that are substantially rigid after forming, such as various plastic materials including but not limited to polyethylene terephthalate (PET), low-density polyethylene (LDPE), high-density polyethylene (HDPE), polypropylene (PP), styrene acrylonitrile (SAN), polyethylene terephthalate glycol (PETG), or other plastic material, or from non-plastic materials, such as glass, stainless steel, ceramic, or various eco-friendly materials (e.g., bamboo-based materials). These rigid components may be manufactured via any suitable manufacturing techniques including but not limited to injection molding, extrusion, additive manufacturing, etc.

Figure 3:
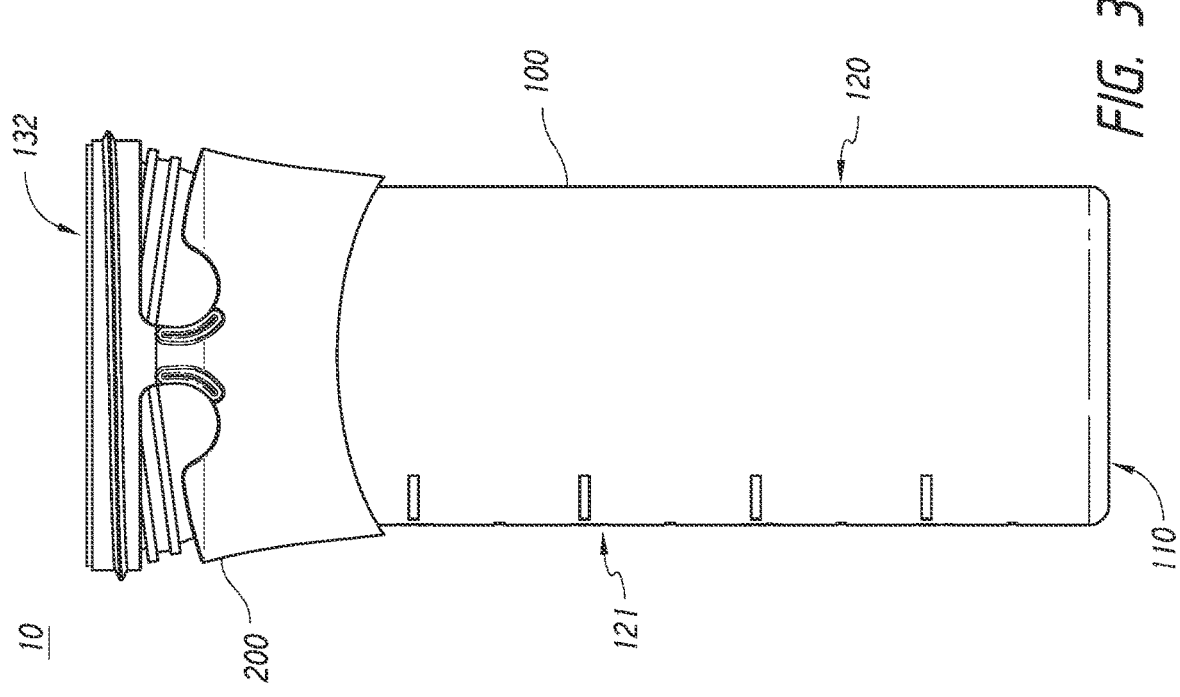
FIG. 3 is a side elevation view of the storage and feeding system in FIG. 1.
Figure 2:
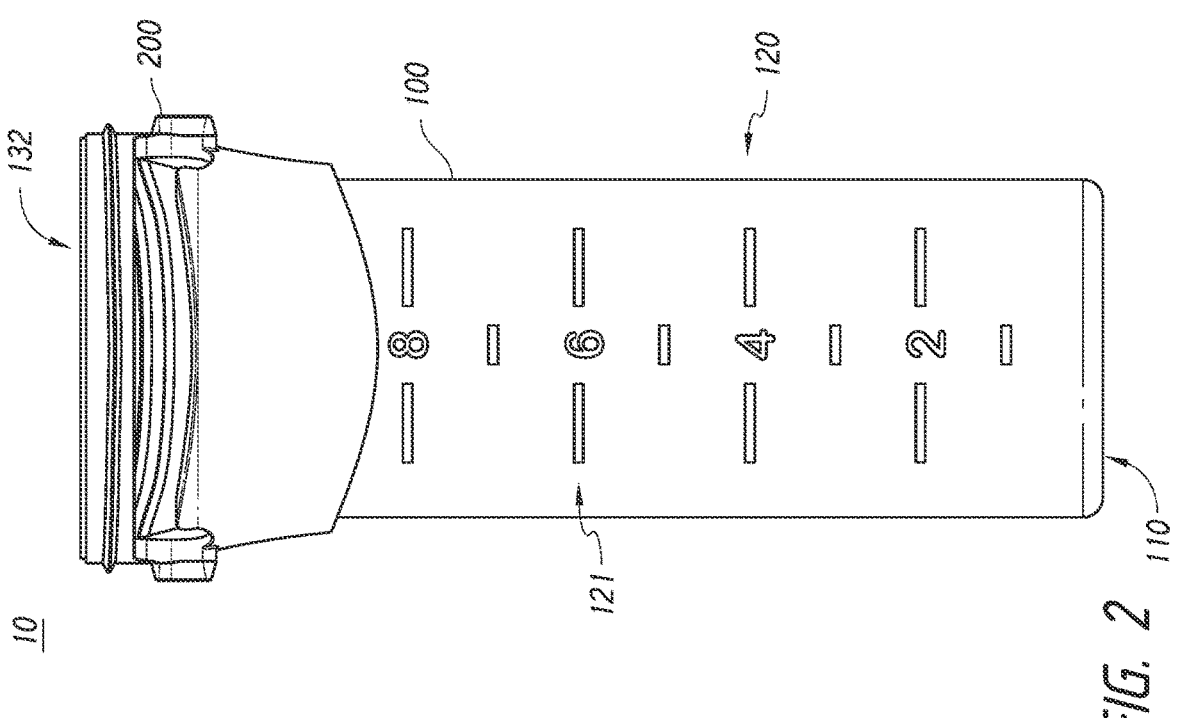
FIG. 2 is a front elevation view of the storage and feeding system in FIG. 1.
Figure 4:
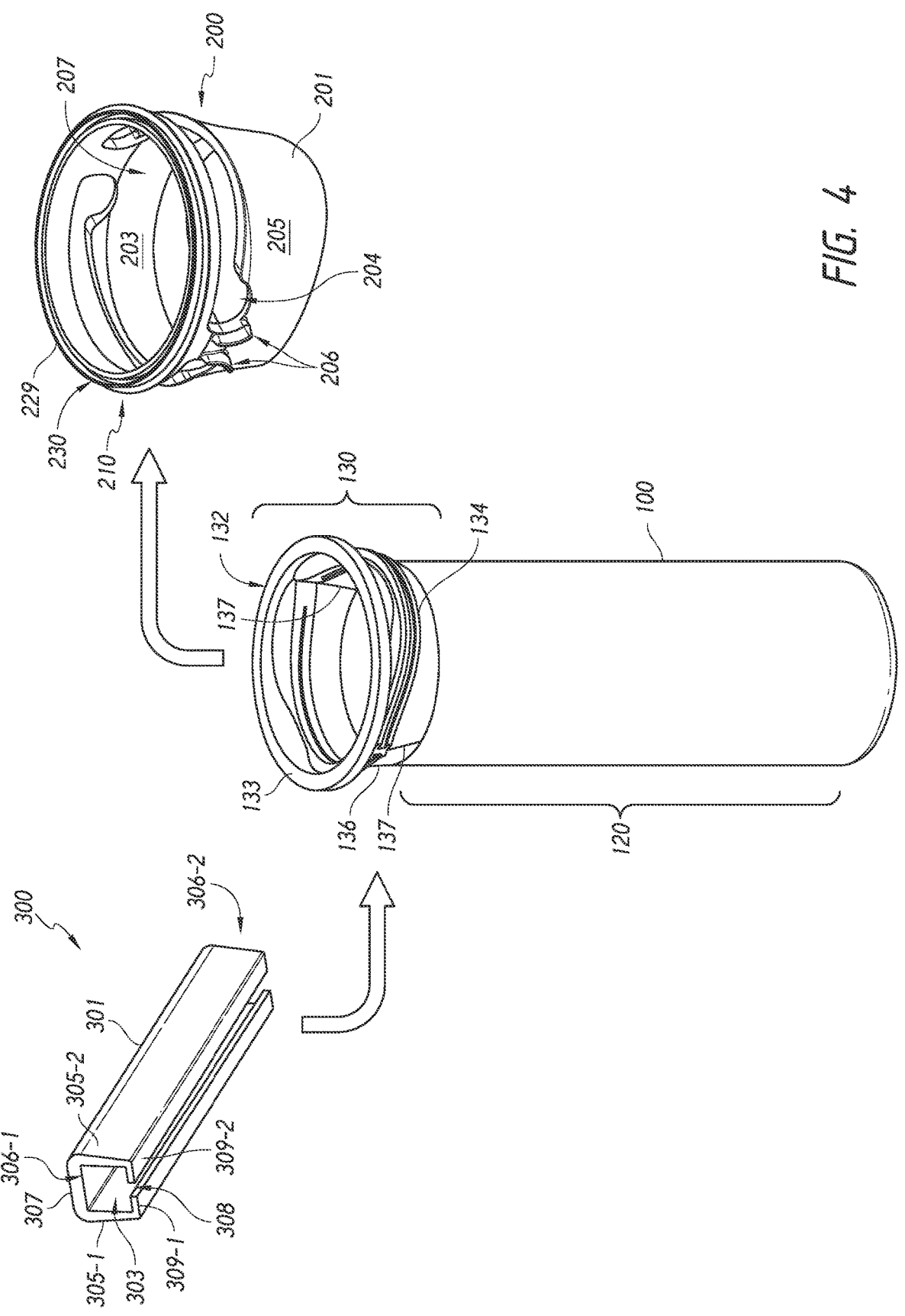
FIG. 4 is an exploded view of the storage and feeding system of FIG. 1, showing the collar removed from the container and further showing the clamp for use in the storage configuration.

Referring now to FIGS. 1-4, components of a breast milk storage and feeding system 10 according to some embodiments of the present disclosure will be described. The storage and feeding system 10 is shown in FIG. 1 in the open configuration, and includes a flexible container 100 and a collar 200 removably attached to the container 100. FIGS. 2 and 3 show front and side views of the system 10 in the open configuration of FIG. 1. FIG. 4 shows the system in a transitional state, with the collar 200 removed from the container 100 prior to reconfiguring the container 100 into the closed configuration. FIG. 4 also shows a clamp 300 for sealing the mouth of the container 100 when in the closed configuration.

Figure 6:
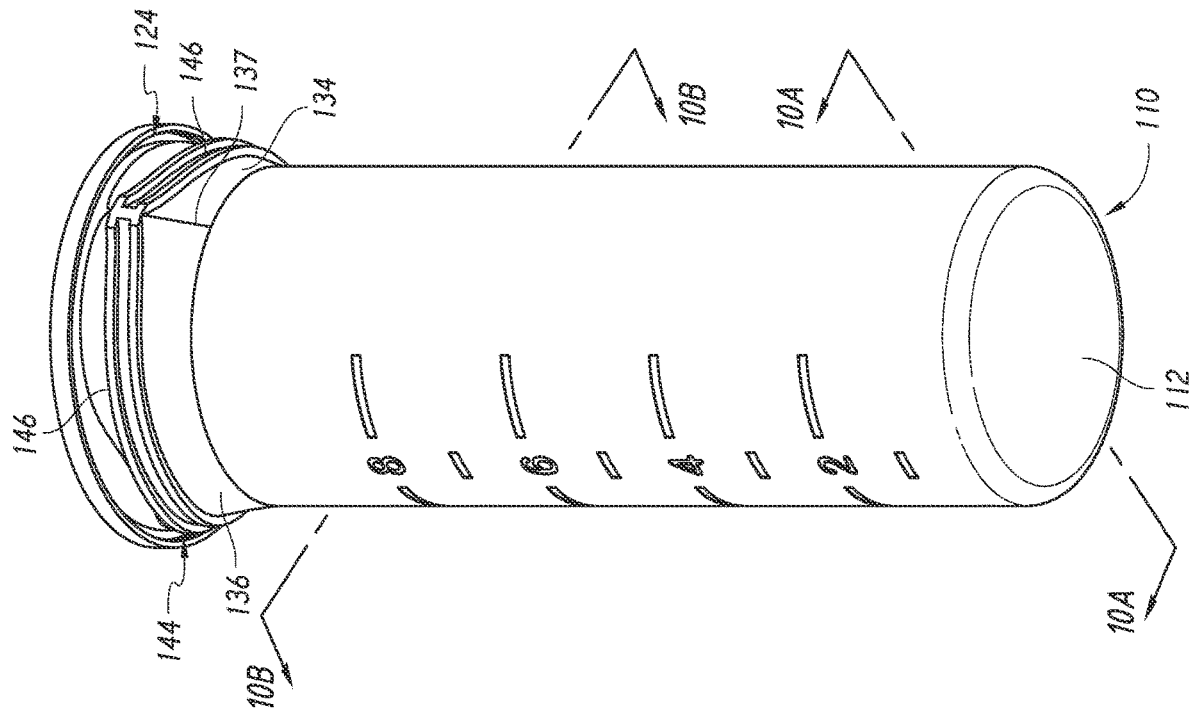
FIG. 6 is a bottom isometric view of the container of FIGS. 1-4.
Figure 10B:
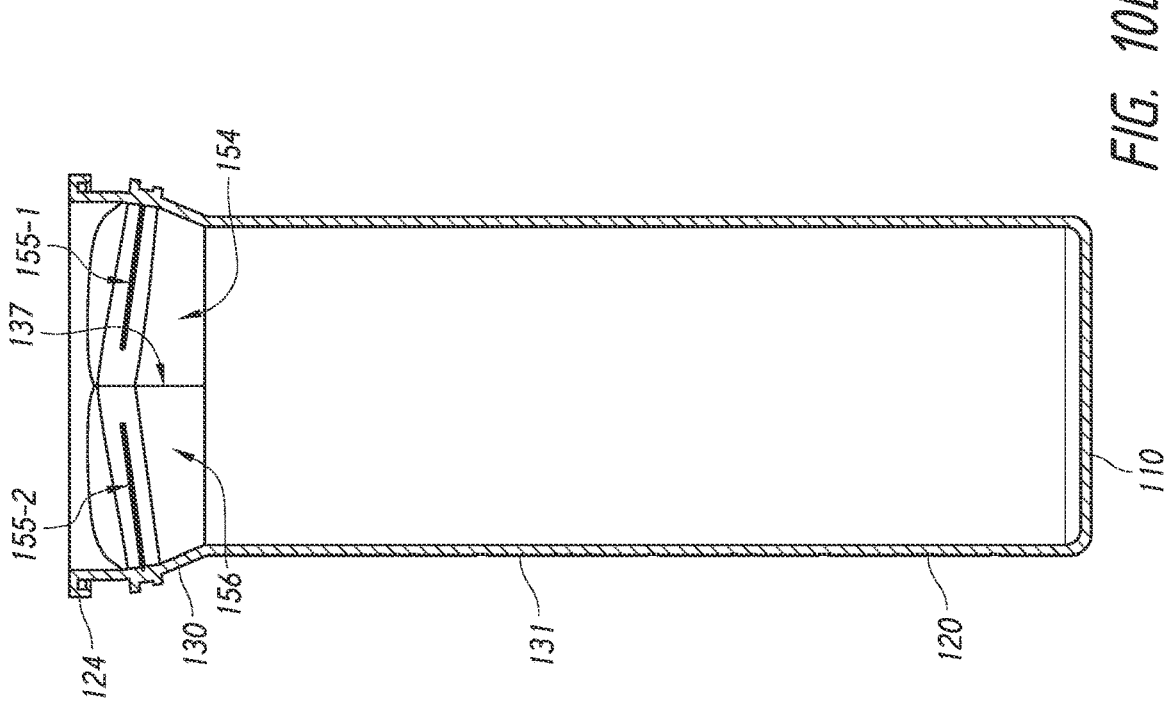
FIGS. 10A and 10B show cross-sectional views of the container taken at lines 10A-10A and 10B-10B, respectively, in FIG. 6.
Figure 10A:
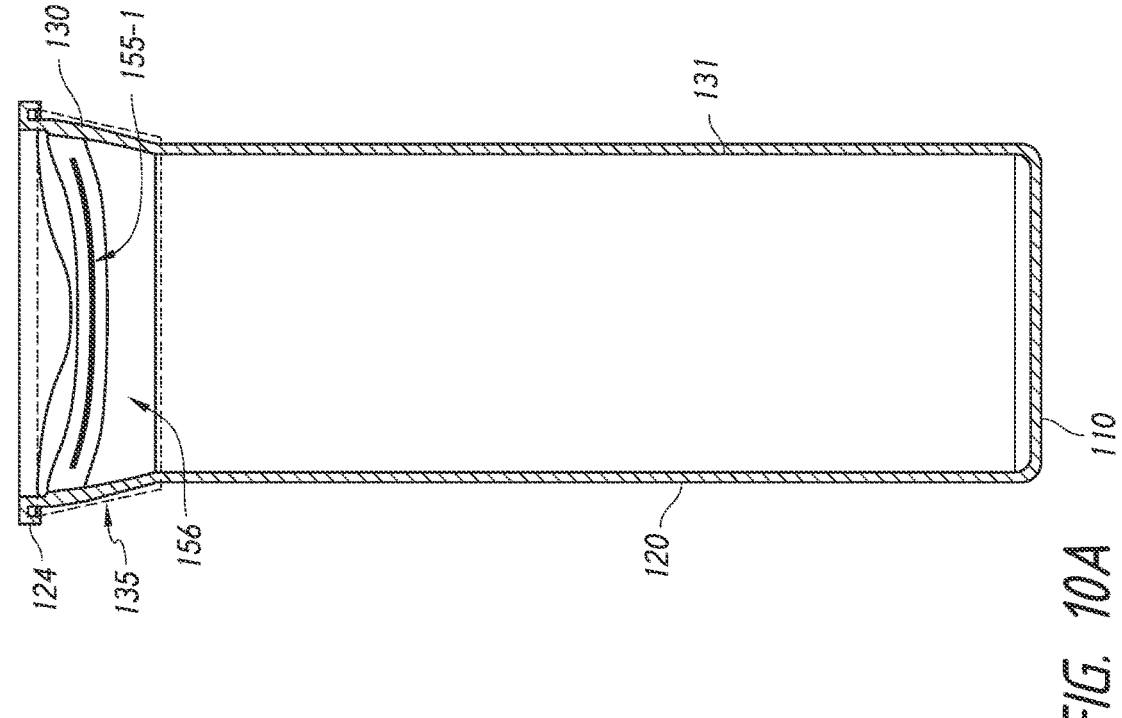
Figure 12:
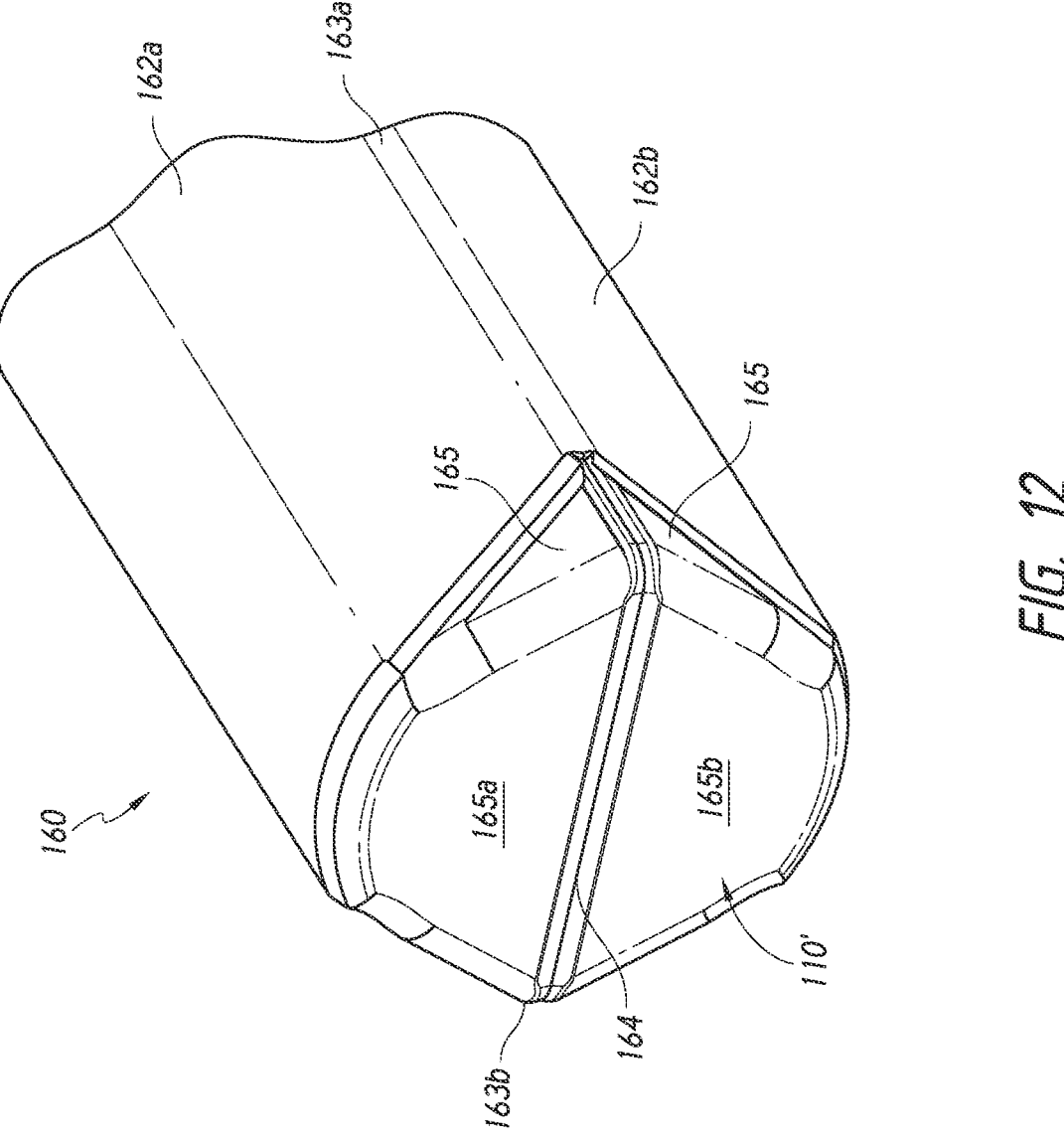
FIG. 12 shows another example of a bottom portion of a multi-use container according to the present disclosure.

As previously mentioned, the container 100 may be flexible and may be entirely, or at least partially, made from a suitable flexible material (e.g., a resiliently deformable material suitable for use with food). Referring also to FIGS. 6, 10A and 10B, the base 110 of container 100 is configured to stably support the container in an upright position onto a surface (e.g., a table, a counter, a shelf). For example, the base 110 may be shaped such that its outward facing surface 112 (see FIG. 6) is substantially flat. In other embodiments, the base 110 may be differently shaped, for example having a central portion that is contoured inward (toward the interior of the container) and a peripheral portion defining a substantially flat annular surface to stably support the container 100. The main body 120 (see FIG. 4) of the container 100 may have a substantially cylindrical shape, which may facilitate ease of manufacture and subsequently, ease of cleaning. For example, the base 110 and main body 120 of the container may be substantially cup-shaped, with the cup having substantially cylindrical walls (see FIGS. 10A and 10B). However in other embodiments, the base and/or main body 120 may be differently shaped. For example, the main body 120 may have a slightly flattened or oval shape, or it may have an irregular, contoured shape, such as having grip features (e.g., finger shaped divots) along the main body. In some examples, the main body 120 or at least a portion thereof (e.g., a bottom portion 160 as shown in FIG. 12) may be configured for foldability, such that the container 100 may be provided in a lay-flat configuration, e.g., when sealed with the clamp 300. In the example in FIG. 12, the bottom portion 160 is generally hexagonal and includes a first side wall 162a and a second sidewall 162b, which are connected along opposing first and second edges 163a and 163b, respectively. The thickness of the material of the bottom portion 160 may be substantially constant such that the edges 163a and 163b create natural folding lines along the length of the container 100. Additionally, one or more weakened portions (or fold lines) 164. The one or more weakened portions (or fold lines) may be provided by a portion of thinner material as compared to other portions of the main body. The one or more weakened portions (or fold lines) 164 may be provided along the bottom portion 160, for example along the base 110′, extending from the first edge 163a to the second edge 163b, thereby providing a fold line at the base of the container 100. In some embodiments, thinner side portions 165 may optionally connect the base to the side walls 162a and 162b to further facilitate the folding of the container 100. When used as a feeding bottle, the container's base is provided in the unfolded configuration in which the base provides a substantially flat, stable surface to support the container upright onto a support surface (e.g., counter or table). When used for storage (e.g., with the mouth sealed by clamp 300), the bottom portion 160 may be provided in the folded (or lay-flat) configuration in which the two halves 166a and 166b of the bottom portion are folded inward towards the interior of the container, along the fold line 164. The shaping of the base and/or main body may thus provide different aesthetics and/or functional benefits. The wall 131 of the main body 120 of container 100 may be transparent or semi-transparent and may include a liquid level indicator (e.g. graduated markings 121) to enable a user to determine the volume of liquid contained therein.

The upper portion 130 of the container 100 includes a mouth 132, which in the open configuration defines a substantially circular opening 133. In some embodiments, the upper portion 130 is configured to facilitate flattening thereof when the container is provided in the storage configuration. For example, the upper portion 130 may be provided by a first side 134 (also referred to a first wall 134) and a second side 136 (also referred to as second wall 136). As shown in FIGS. 4, 6 and 10A-13, in some embodiments, each of the two sides 134 and 136 is provided by a substantially trapezoidal wall (approximate outline of which is shown by phantom line 137 in FIG. 10A). Each of the trapezoidal walls 134 and 136 is arranged with its narrower side facing the base of the container 100. The lower, narrower portions of the trapezoidal walls are attached to (e.g., integrally formed with) top edge of the main body, with each side wall spanning approximately half the circumference of top edge of the main body 120. The respective side edges of the trapezoidal walls meet and join at a respective one of the two opposing interfaces 137. The interfaces 137 form a pair of creases at substantially radially opposite locations along the perimeter of the upper portion 130 of the container 100. In some embodiments, each of the creases may be defined by an internal and/or external discontinuity (or apex). In some embodiments, this discontinuity or apex is defined by a sharp or pointed edge along the outer surface and a corresponding sharp or pointed trough on the internal surface that form an outwardly pointing crease at the location of each of the two interfaces 137. In other embodiment, the apex may be rounded but a discontinuity in an otherwise relatively smoothly contoured periphery of the container may be marked by a substantial change in the radius (e.g., a much tighter radius marking the crease of interface 137). Any other suitable contouring may be used for forming a crease at each of the interface 137 between the opposing walls 134 and 136, such as by the use of a weakened portion (e.g., along the interior), may be used. As noted, the creases are generally radially opposed to facilitate the forming of respective edges when the upper portion is flattened by the bringing of the two walls together. The upper portion 130 of the container 100 of the present example is outwardly tapered (i.e. the diameter of the opening 133 is larger than the lower end of the upper portion), and thus the interfaces 137 (e.g., creases) fan outward from the lower edge of the upper portion toward the opening 133. In other embodiments, a different configuration of the upper portion may be used, e.g., which does not include generally trapezoidal walls and/or creases therebetween. For example, the container, or at least the upper portion, may be generally oval (or elliptical) in cross-section (transverse to the length of the container). In some such embodiments, the folding may be facilitated by pressing the two opposing sides of the container that lie on the opposite sides of the long axis. In other embodiments, the upper portion may be substantially cylindrical. Various other configurations may also be used.

Two coupling interfaces are provided in the upper portion 130 of the container 100. Referring again to FIG. 6 and now also to FIGS. 8A-8B and 9, a first coupling interface 124 is defined at the mouth 132 and is configured to removably coupling the collar 200 to the container 100. The first coupling interface 124 includes a ledge 126 extending radially outward from the opening 133 of the mouth 132, and a lip 128 protruding downward from the ledge 126 (see FIG. 9). The first coupling interface 124 may be integrally formed with, from the same material as, the upper portion 130. The first coupling interface 124, and specifically the ledge 126, may thus define the top surface of the container 100 when assembled with the collar 200, and the collar 200 is positioned below the top surface of the container 100. In use, e.g., when connected to an accessory (e.g., a connector or adapter of a breast pump or a feeding accessory such as a bottle nipple), this top surface seals against the accessory, eliminating any contact of between the liquid being deposited into or dispensed out of the container (e.g., breast milk) and the collar, which may be made from BPA or phthalate containing plastic.

Figure 5A:
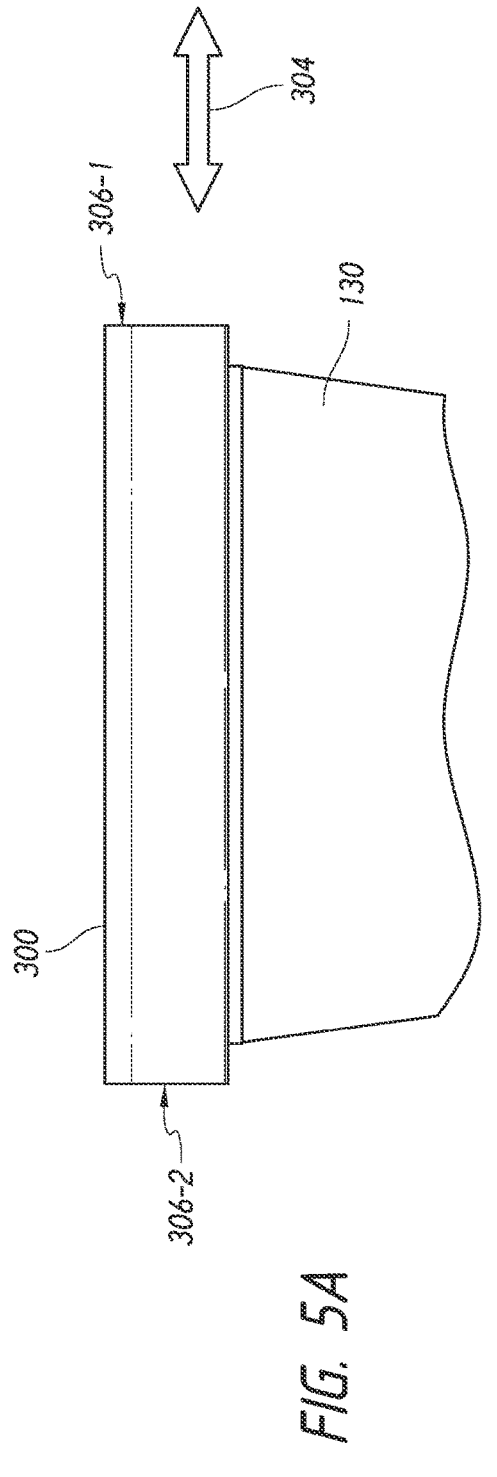
FIG. 5A is an elevation view of a top portion of the container of FIG. 4 with clamp attached thereto, providing the container in the storage configuration.
Figure 5B:
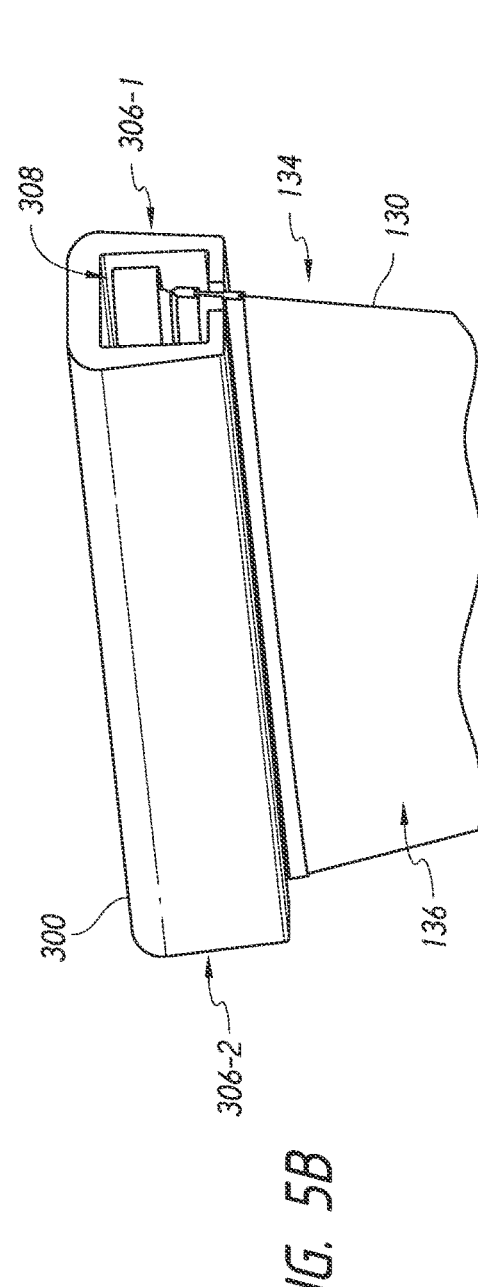
FIG. 5B is another, perspective view of the container portion shown in FIG. 5A.

The second coupling interface 144 provided in the upper portion 130 is located below the first coupling interface 124. The second coupling interface 144 is configured to engage (e.g., interlock with) the clamp 300. For example, the second coupling interface 144 may define a respective groove 146 on each of the outward facing sides of the opposing walls 134 and 136. The groove 146 may be defined by any suitable manner or structure, such as by a pair of spaced apart ridges protruding above the outer surface and which define a channel between or by a groove/channel being formed below surface. Each of the grooves 146 may extend substantially the full length between the two creases provided by the opposing interface 137. The grooves 146 may follow any suitable path between the two creases, e.g., curving downward (see FIGS. 8A and 8B), such that the grooves lie in a substantially straight line that extends substantially horizontally when the upper portion 130 is flattened (see FIG. 5A). As described at least the upper portion 130 of the container 100 is sufficiently resiliently deformable such that it can be flattened, by bringing the two opposing walls 134 and 136 of the upper portion 130 together, thereby closing the mouth 132 and providing the container 100 in the closed configuration. The material from which container 100 (or at least upper portion 130) is made is sufficiently soft or pliable such that it can be easily flattened by the user with one hand. Once provided in the closed configuration (i.e. with the two walls 134 and 136 brought together), the clamp 300 is used to secure the two walls 134 and 136 of the upper portion 130 together, as shown in FIGS. 5A and 5B.

Referring also to FIGS. 10A and 10B, the inward facing surfaces 154 and 156 of the opposing side walls 134 and 136 may include surface sealing features 155 (e.g., a recess, a protrusion, or a combination of the two) for providing a better seal when the two surfaces 154 and 156 are in contact with one another in the storage configuration. In some embodiments, the surface sealing features 155 may include a first sealing feature 155-1 (e.g., one or more first ridges) on one of the two surfaces 154 and 156 and a second sealing feature 155-2 (e.g., one or more second ridges) on the other of the two surfaces 154 and 156. In some embodiments, the two sealing features 155-1 and 155-2 are both implemented as one or more ridges, which may be slightly misaligned from one another, such that when the upper portion is flattened, with two sides together, the applied force (e.g., by the user and subsequently the holding force of the clamp) may force the two ridges to abut (e.g., one slightly above the other) and/or compress to form a seal. In other embodiments, the first and second sealing features 155-1 and 155-2 may be implemented as one or more protrusions on one of the two surfaces and at least one groove on the opposite surface, positioned and sized to receive the protrusion, whereby interlocking of the two sealing features 155-1 and 155-2 when the two sides 134 and 136 are brought together forms a seal. In some embodiments, the sealing features 155-1 and 155-2 may remain interlocked with one another after the applied force (e.g., the user squeezing the two sides 134 and 136 together) is released. In such embodiments, the use of the clamp 300 may ensure that the two sides 134 and 136 do not inadvertently come apart during storage. The clamp 300 may thus facilitate a more secure and leak-proof, air tight, closure of the container 100. In other embodiments, the sealing features 155-1 and 155-2 may remain interlocked only with the application of external force (e.g., by the user's hand and/or the clamp 300). In some embodiments, the sealing features 155 (e.g., one or more ridges and/or interlocking grooves) extend substantially transversely to the mouth 132 (see FIG. 1) and may span substantially the periphery of the interior of the mouth 132. In some embodiments, the sealing features 155-1 and 155-2 on the interior surfaces may substantially align with the respective groove 146 on the exterior surfaces of walls 134 and 136. In some such examples, the sealing features 155-1 and 155-2 may follow a similar path to the contour or path of the respective groove 146 on the respective outer surface. In some embodiments, the sealing feature 155 is so positioned on the interior surface so as to lie between the walls or protrusions that define the respective groove, albeit on the opposite surface of that wall. Alignment between the sealing features 155 and the grooves 146 may facilitate a better seal of the container 100, e.g., by the force applied by the clamp 300 positioned within the groove, when the container 100 is in the closed configuration.

Figures 7A, 7B, 8A, 8B:
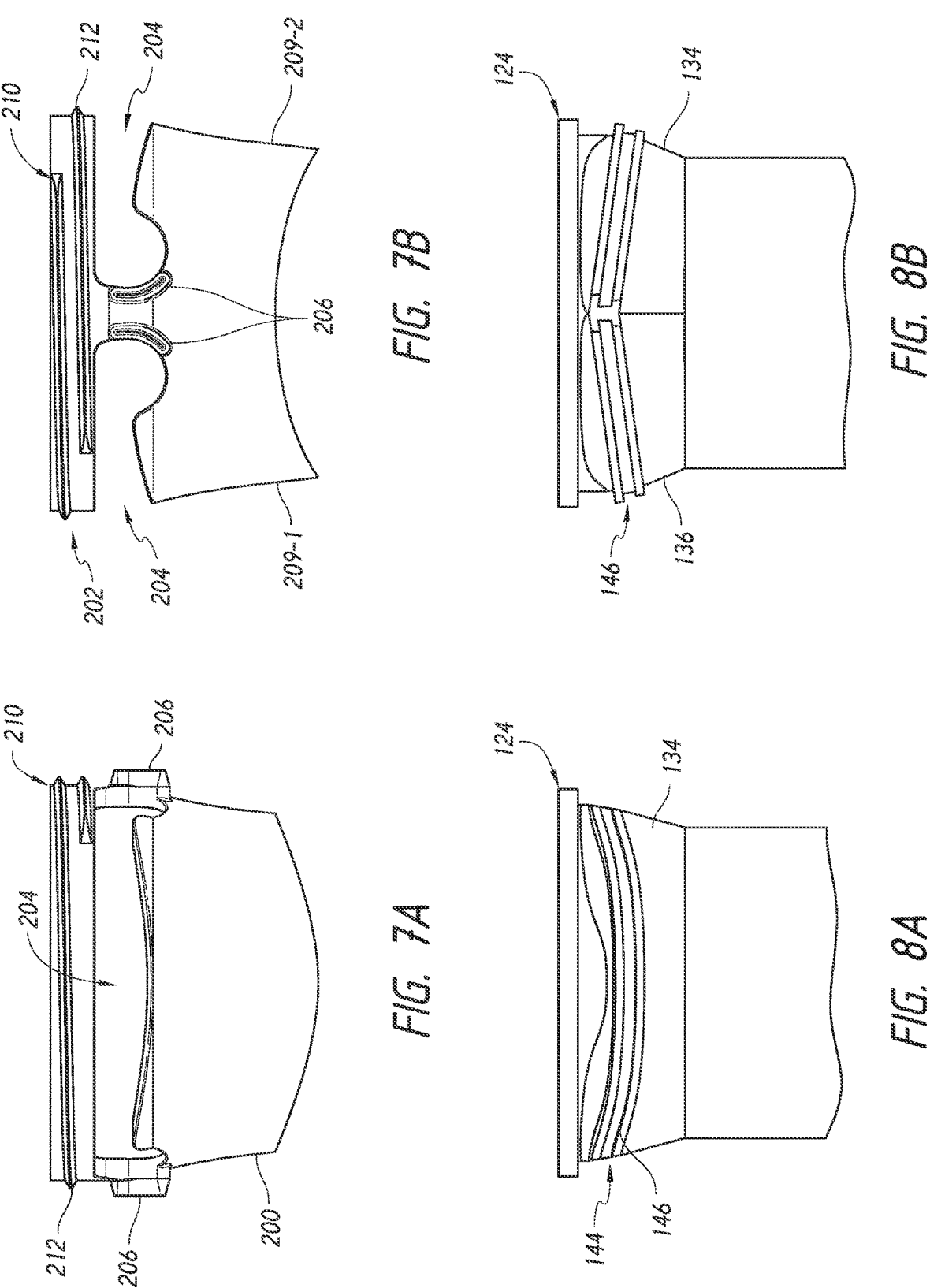
FIGS. 7A and 7B show front and side elevation views of the collar of the storage and feeding system shown in FIGS. 1-4.
FIGS. 8A and 8B show front and side elevation views of the top portion of the container of the storage and feeding system shown in FIGS. 1-4.
Figure 9:
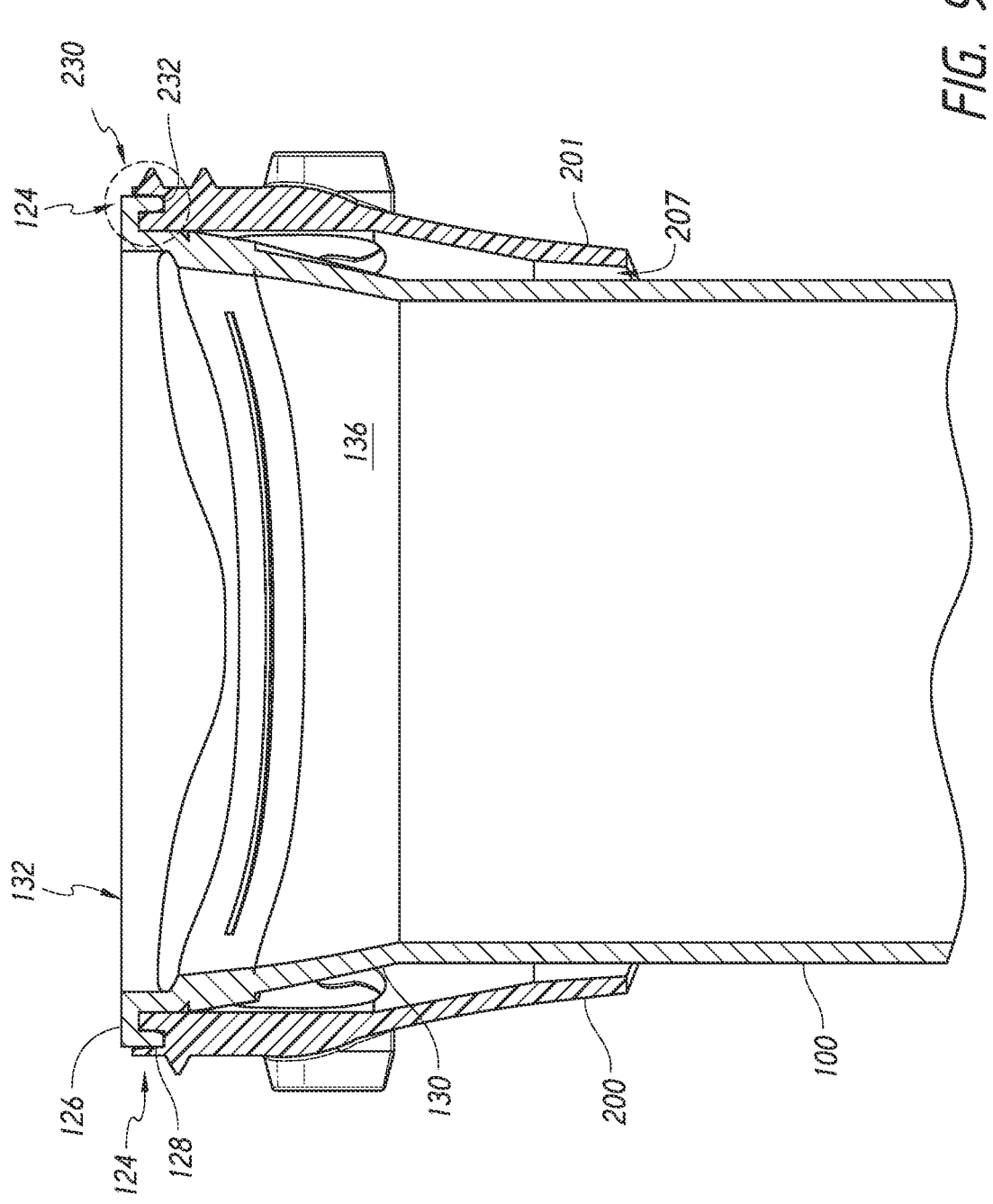
FIG. 9 shows a cross-sectional view of a top portion of the container and collar attached thereto, taken at line 9-9 in FIG. 1.

Referring now also to FIGS. 7A-7B and 9, the collar 200 provides another coupling interface 210 for removably, mechanically connecting the container 100 to an accessory (e.g., a mechanical connector/adapter of a breast pump or a feeding accessory, such as a bottle nipple/collar combination). The collar 200 may be implemented by a substantially rigid component or body 201, which may be integrally formed, for example by injection molding, machining, 3D printing, or being otherwise formed as a monolithic/integral body. The body 201 is suitably shaped such that it can accommodate (e.g., by being sleeved over) the upper portion 130 of the container. For example, the body 201 may have a generally cylindrical or frustoconical, annular shape defined by interior and exterior walls 203 and 205, respectively, and forming a passage 207, sized to accommodate the upper portion 130 at least partially therein. Depending on the overall shape of body 201, the body 201 may define a pair of through cutouts 204, one located on each of the opposing sides 209-1 and 209-2 of the body 201, which may accommodate one or more features of the upper portion 130 (e.g., at least part of the second coupling interface 144) through the cutouts (see FIG. 3). The cutouts 204 are arranged on the body 201 to substantially align with the underlying feature (e.g., the coupling interface 144) of the container 100. The cutouts 204 may be may be contoured (e.g., curved) in a corresponding manner to the contour of the underlying feature of the container (e.g., the grooves 146) and/or for aesthetic purposes. In some embodiments, the lower edge 208 of the body is contoured, for example defining a substantially sinusoidal curve (see also FIGS. 2-3), which may provide one or more utilitarian (e.g., a larger gripping surface for handling the collar for example during installation/removal) and/or aesthetic benefits. The body 201 may include one or more protrusions 206, also referred to as grips, that project outwardly from the surface of the body 201. The grips may be anywhere suitably located to facilitate gripping by the user during installation of the collar 200. For example, at least one grip 206 may be provided at each of two radially opposite locations of the collar, in the present example a pair of grips 206 is shown at each location, adjacent with the terminal ends of the cutouts 204.

The body 201 includes a first collar coupling interface 230 for coupling the collar 200 to the container 100 and a second collar coupling interface 210 for coupling the collar 200, and thus the container 100, to an accessory. The first collar coupling interface 230, is provided at the upper edge or rim 229 of the collar 200. Referring to FIG. 9, the first collar coupling interface 230 may be implemented by a circumferential (e.g., annular) groove or slot 232, extending along the top (or rim) surface of the body 201. The groove 232 may be implemented as a blind opening terminating within the thickness of body 201 or as a through opening passing through the thickness of the upper portion of the body 201. The annular groove 232 is sized to receive, preferably for an interference fit with, the lip 128 of the first coupling interface 124 of the container 100. The second collar coupling interface 210 may is implemented, in some embodiments, as a thread 212, on the outward facing side 202 of the body 201. The coupling interface 210 (e.g., thread 212) may be located near the upper edge of the body 201, as shown in the example in FIGS. 7A and 7B. In other embodiments, the coupling interface 210 (e.g., thread 212) may be elsewhere along the vertical elevation of the collar body 201. The coupling interface 210 may be provided in any suitable configuration (e.g., a thread of a particular shape, having a particular root, crest, angle, pitch, etc.) to cooperatively mate with the thread or other coupling interface (e.g., a snap interface) of the desired accessory (e.g., a breast pump or nipple/collar combination for bottle feeding).

Like the collar, the clamp 300 may be substantially rigid. Referring to FIGS. 4, and 5A-5B, the clamp 300 may be implemented as a substantially elongate body 301 forming a U-shaped channel 303. Longitudinal side walls 305-1 and 305-2 extend from opposite lengthwise edges of the top wall 307, each of the side walls terminating at respective lip 309-1 and 309-2. Lip 309-1 and lip 309-2 extend toward one another narrowing the opening 308 of the U-shaped channel 303. The elongate body 301 has open first and second longitudinal lends 306-1 and 306-2, allowing the clamp 300 to be slid into engagement with the container 100, from one side of the flattened upper portion 130 toward the other, as shown by arrow 304 in FIG. 5A, with the grooves 146 of the container 100 guiding the position of the clamp 300 on the upper portion 130. In other embodiments, the elongate body 301 may have only one open longitudinal end (e.g., either longitudinal end 306-1 or longitudinal end 306-2) to enable the sliding of the clamp 300 onto the container 100. Each of the grooves 146 receives a respective one of the lips 309-1 and 309-2 and secures the clamp 300 into engagement with the container 100. Similarly, removal of the clamp 300 involves sliding the clamp 300 out of engagement with the upper portion 130 of the container 100, the sliding out similarly guided by the grooves 146. The clamp 300 is formed by any suitable material (e.g., a rigid plastic, metal, composite, ceramic, wood, wood or other fiber based products such as bamboo, etc.) that can apply sufficient force to maintain the seal formed by the upper portion 130 of the container 100 when in the storage configuration.

In use, the container 100 is provided in the open configuration (see FIG. 1) and is connected to a breast pump adapter, e.g., via the coupling interface 210 of the collar 200. Breast milk can thus be pumped directly into the container 100. After the breast milk is collected in container 100, it is disconnected from the breast pump adapter. The container 100 may then be used for feeding with the collar 200 or another collar having a different coupling interface 210 installed to enable coupling the container to the breast feeding accessory (e.g., a nipple and collar combination). Alternatively, the collar 200 may be detached from the upper portion 130 of the container 100 (see FIG. 4) and the container 100 may be provided in the closed configuration by flattening the two sides 134 and 136 and sealing the mouth 132 of the container. The clamp 300 (see FIG. 4) may be installed (e.g., through a sliding engagement with the coupling interface 144, as shown in FIGS. 5A and 5B) on the top portion of the container to ensure a leak-proof, in some cases substantially air tight, seal. The container 100 is now ready for storage in any desirable location (e.g., freezer) and in any desirable orientation (e.g., laying on its side or even upside down). To use the liquid stored in the container 100, a similar process may be performed in reverse, whereby the clamp 300 is removed from the upper portion 130 and the container 100 is reconfigured to the open configuration by opening the mouth 132 to its substantially round state. The contents (e.g., breast milk, which may be frozen) may be reheated by submerging at least a portion of the container 100 in hot water and/or by heating the contents in the container via a different method (e.g., by leaving the container 100 at room temperature or putting it in a bottle warmer). Depending on the method used for re-heating the breast milk, the heating may be performed before or after the container 100 is provided in the open configuration. For example, the container 100 may remain in the closed configuration if heating by submerging in water, or the container 100 may be opened (e.g., the clamp 300 removed and/or mouth 132 opened) if reheating in a microwave. Regardless, the contents can remain within the container 100 during any desired/suitable heating method. A collar 200 having the desired coupling interface 210 (e.g., a thread suitable for connecting the container to the desired accessory) can be attached to the coupling interface 124 of the container 100 to now enable its use as a feeding bottle. After use (e.g., after depositing, storing, reheating, feeding breastmilk, or any combination thereof) the container, collar and/or clamp may be cleaned (e.g., in a dishwasher or by hand) for future use. It should be further noted that the container 100 may also be used for storage and feeding of other types of liquids or semi-liquids, such as juices, purees, etc., for example as a child grows up. In such use cases, the collar 200 with a suitable coupling interface 210 for coupling the container to a suitable feeding accessory may be used, or the container 100 may be used without a collar simply as a cup to hold the liquid or semi-liquid food. For example, as shown in FIG.

11B, the container 100 may be coupled to a bottle cap 404 with a dispenser tip (or spout) 406 and optional lid 408. The bottle cap may be formed of more rigid material than the flexible material typically used for feeding nipples and as such the spout may be configured to generally retain its shape during use. However, it will be understood that bottle caps with flexible spouts may also be operatively coupled to the container and in some cases, the container may be provided to a user as a kit, including one or more containers, at least one collar, and a plurality of differently shaped bottle caps that fit the provided collar(s). Bottle caps of virtually any type of configuration (e.g., with a dispenser spout of any suitable shape and size/aperture) may be coupled to the collar thereby increasing the multi-functionality of the container 100.

As described, the container 100 may be made, in some embodiments, from food-grade silicone, which is microwave safe. The container 100 and other components of system 10 are made from materials sufficiently durable and capable of being cleaned numerous times (over 10, 50, 100 times, in some cases) and thus a single container and one or more collars can provide a reusable and multi-purpose storage bag and feeding bottle all in one, eliminating the need for different containers, and the transfer of milk between containers, during the various stages of the breast feeding process.

It will be understood that any one of the examples, embodiments or processes described herein may, unless stated otherwise, be combined with one or more other examples, embodiments and/or processes or be separated and/or performed amongst separate devices or device portions in accordance with the present systems, devices and methods. Finally, the above-discussion is intended to be merely illustrative of examples and should not be construed as limiting the appended claims to any particular embodiment or group of embodiments. Thus, while the present invention has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A breast milk storage and feeding system comprising:
   a flexible container having a base configured for stably supporting the flexible container onto a support surface and an upper portion defining a substantially circular mouth when the flexible container is in an open configuration, wherein the upper portion is resiliently deformable into a storage configuration in which opposing sides of the upper portion are in contact with one another thereby sealing the mouth of the flexible container, and wherein the upper portion comprises a first coupling interface proximate the mouth of the flexible container for removably connecting a collar thereto when the flexible container is in the open configuration, and a second coupling interface below the first coupling interface for removably connecting a clamp thereto when the flexible container is in the storage configuration;
   a collar made from a substantially rigid material and configured to be removably coupled to the first coupling interface, the collar comprising a third coupling interface on an outward facing surface thereof, the third coupling interface configured for mechanically coupling the flexible container, via the collar, to a breast pump or a feeding accessory; and the clamp configured to removably slidably engage the second coupling interface for sealing the opening of the flexible container when in the storage configuration; wherein, the upper portion tapers toward the mouth of the container, the upper portion defines a pair of creases at radially opposite locations, the second coupling interface comprises a pair of grooves, each extending along a respective one of the opposing sides of the upper portion, between the pair of creases, and the collar comprises a pair of cutouts that align with the pair of grooves.

2. The system of claim 1, wherein the container has a substantially flat circular base.

3. The system of claim 1, wherein the container has a substantially flat hexagonal base comprising a weakened portion along a length of the base.

4. The system of claim 1, wherein each of the grooves is curved such that its convex side faces the base.

5. The system of claim 1 further comprising a sealing feature on an inward facing surface on each of the opposing sides of the upper portion.

6. The system of claim 5, wherein the sealing feature aligns with the respective groove.

7. The system of claim 1, wherein the first coupling interface comprises a ledge extending radially outward from the mouth and a lip projecting downward from the ledge towards the base.

8. The system of claim 1, wherein the collar comprises a groove along a rim of the collar configured to interferingly receive a lip.

9. The system of claim 8, wherein the flexible container is made from food-grade Silicone.

10. The system of claim 1, wherein at least one of:

the flexible container is made from a material free of Bisphenol A and Phthalates; and the clamp, the collar or both are made from a rigid plastic, composite, or metal.

11. The system of claim 1, wherein the third coupling interface comprises a thread configured for coupling the collar to a thread of at least one of:

a bottle nipple collar; and a breast pump adapter for a breast pump.

12. A kit comprising the flexible container and the clamp of the system of claim 1 and a plurality of the collars of the system of claim 1, each collar of the plurality of collars comprising a third coupling interface provided by a different type of thread for coupling the collar to different types of accessories.

* * * * *